(12) United States Patent
Wang

(10) Patent No.: US 10,477,882 B1
(45) Date of Patent: Nov. 19, 2019

(54) VEGAN MEAT REPLACEMENT FOOD PRODUCT

(71) Applicant: SOPHIE'S KITCHEN, INC., Sebastopol, CA (US)

(72) Inventor: Yao-Hsin Wang, Sebastopol, CA (US)

(73) Assignee: SOPHIE'S KITCHEN, INC., Sebastopo, CA (US)

( * ) Notice: Subject to any disclaimer, the term of this patent is extended or adjusted under 35 U.S.C. 154(b) by 0 days.

(21) Appl. No.: 14/697,482

(22) Filed: Apr. 27, 2015

Related U.S. Application Data

(60) Provisional application No. 61/984,644, filed on Apr. 25, 2014.

(51) Int. Cl.
| | |
|---|---|
| A23J 3/00 | (2006.01) |
| A23L 1/214 | (2006.01) |
| A23L 1/00 | (2006.01) |
| A23L 1/305 | (2006.01) |
| A21D 2/36 | (2006.01) |
| C12P 1/02 | (2006.01) |
| A23L 7/104 | (2016.01) |
| A23L 33/185 | (2016.01) |
| A23J 3/14 | (2006.01) |
| A23J 3/22 | (2006.01) |

(52) U.S. Cl.
CPC ............ *A23L 1/2147* (2013.01); *A21D 2/366* (2013.01); *A23J 3/14* (2013.01); *A23J 3/227* (2013.01); *A23L 1/0076* (2013.01); *A23L 1/3055* (2013.01); *A23L 7/104* (2016.08); *A23L 33/185* (2016.08); *C12P 1/02* (2013.01); *A23V 2002/00* (2013.01)

(58) Field of Classification Search
CPC ...... A23J 3/18; A23J 3/227; A23J 3/32; A23J 3/14; A23J 3/26; A23L 33/185; A23L 7/104; A23L 13/00; A23L 13/426; A23L 13/42; A23L 33/125; A23L 33/17; A23L 33/24; A23L 13/422; C12P 1/02; A23V 2002/00
USPC .... 426/72, 643, 540, 541, 92, 656, 650, 601
See application file for complete search history.

(56) References Cited

U.S. PATENT DOCUMENTS

| | | | |
|---|---|---|---|
| 2008/0254167 A1* | 10/2008 | McMindes | A23J 3/16 426/72 |
| 2009/0047397 A1* | 2/2009 | Tang | A21D 2/183 426/273 |
| 2010/0015318 A1* | 1/2010 | Ito | A23L 1/05 426/574 |
| 2013/0243925 A1* | 9/2013 | van Lengerich | A23L 29/212 426/560 |

OTHER PUBLICATIONS http://greenmerchantdirect.com/sophie-s-breaded-vegan-shrimp-9-packs-8-8-oz-3.html , May 9, 2012; accessed May 1, 2019 (Year: 2012).*

* cited by examiner

*Primary Examiner* — Subbalakshmi Prakash
(74) *Attorney, Agent, or Firm* — Gearhart Law LLC

(57) ABSTRACT

A meat replacement product is provided for elimination diets including vegan diets. Pea protein is combined with konjac and fenugreek. The combination is then subjected to high pressure and temperature in conjunction with an extrusion and texturization process. The resulting product can be used to provide a variety of meat replacements including meatless fish sticks, meatless tuna, and meatless salmon as well as replacements for beef and chicken.

3 Claims, 2 Drawing Sheets

VEGAN MEAT REPLACEMENT FOOD PRODUCT

FIELD OF THE INVENTION

This invention relates to specialty natural food products for elimination diets including vegan diets and, in particular, to meat-replacement food products within the context of a vegan diet and processes for producing such products.

BACKGROUND OF THE INVENTION

Vegan products require that no animal products be used in their production, thus eliminating all meat, eggs, and all dairy ingredients such as milk or butter. Vegans eat only plant-based foodstuffs. Vegans avoid all animal products often for ethical reasons concerned with the treatment and killing of animals. However, concerns about food safety, health, nutrition, and climate change also influence the emerging movement toward vegan products in the marketplace.

To date, elimination diet products, such as vegan products, have turned toward soybeans and soy-based substances to provide the ingredients that are necessary to make meat replacement products palatable or to give them a meat-like texture or appearance. However, because of the increasing prevalence of soy ingredients in vegan products, and the rise of genetically modified soybeans in the food supply, many vegans have experienced both negative physical reactions to soy ingredients in the form of allergic reactions or symptoms of soy intolerance, and social and moral antipathies to GMO products per se. The increasingly high demand for soybeans has led to the introduction of GMO soybeans to meet that demand. One report suggests that 90% of U.S. soy production today is of GMO soy.

Demand for vegan meat replacement products that are not made with either GMO ingredients or soy ingredients has not met with satisfactory solutions. This invention sets forth a new vegan meat replacement platform that avoids both soy and GMO ingredients.

SUMMARY OF THE INVENTION

The invention arises from the needs for non-GMO, non-soy, vegan meat replacement food products, and is based upon the use of non-traditional ingredients and novel proprietary food processes and methods for making vegan meat-replacement products. While there are vegan meat-replacement products in the marketplace, most of them use soy to create a meat-like texture. But as soy becomes a popular food ingredient in many alternative foods and beverages, consumers often find themselves consuming too much soy, which can precipitate bodily reactions, and growing weary of its characteristic taste and texture. In addition, its predominance in the food supply has given rise to a number of allergies and intolerances, and this is particularly true with vegan products. Soy allergies are among the top 10 allergies in the U.S. The increasing demand for soy ingredients has made it difficult to find non-GMO soy, so consumers who require vegan products and non-GMO products are often left without good alternatives.

This invention introduces new ways to create non-GMO, non-soy vegan meat replacement products and involves three central components and associated processing that work together to allow the creation of multiple non-GMO, non-soy, vegan meat-replacement products (e.g., burgers and fillets). They are: i) the use of konjac (*Amorphophallus rivieri*), an Asian plant that is little-utilized in most of the world, to provide an alternative binding agent, ii) the use of pea protein (*Pisum sativum*) in a novel process to supplant soy based proteins and to provide a substance that can be extruded to form a meat-like texture, and iii) the use of fenugreek (*Trigonella foenum-gracecum*) to embed suitable plant protein into the konjac and pea protein mixture to provide a meat replacement that can be a source of protein in a vegan diet. The result is an entirely plant-based, vegan, gluten-free, dairy-free, soy-free, and non-GMO food.

1. The Role of Konjac Root

Konjac is a large East Asian flowering plant that has been used in Asia to make certain food products. To this day, it is used in Asia to make vegetarian foods, however it is largely unknown outside of East Asia. In this invention, konjac is deployed as a binding agent for textured plant protein. In the context of the present invention, konjac is used as a replacement for whey protein (a dairy product) or yeast extracts, that are often GMO, to bind the plant base protein. In the invention the traditional soy-based processes are changed and konjac flour is used to bind the plant base protein. As well, konjac is high in fiber, so it also helps boost the overall fiber content of the products.

2. The Use of Pea Protein to Supplant Soy Ingredients

At the present time almost all meat replacement products use soy to give them the meat-like texture. In food science, soy is perfect for this purpose because it texturizes so easily. However, in the present invention the process is changed from the common practice to introduce pea protein as a texturizing source. Pea has very short fibers and is not as sticky as is soy. Therefore, it is hard to extrude, but the present invention, through a process of time, heat, and pressure, transforms the mixture into a substance that can be extruded to create a textured pea protein.

Originally, the inventor found it to be impossible to create a mixture that could be extruded, but in time and through experimentation, the inventor discovered a method that made the mixture extrudible. The method involves preparing pea protein to meet certain specifications that, when submitted for a certain length of time to a certain temperature and pressure produces an extrudible end product that produces small crumbs that can be formed into burgers and fillets. The pea protein mixture then can be used to make vege-burgers or vege-fillets, such as fishless sticks, vegan smoked salmon, or even a canned vegan tuna substitute with no soy.

3. The Use of Fenugreek to Embed Protein

Because konjac is mostly fiber and zero protein, it is desirable to bring a protein source into the meat replacement products. Therefore, in order to make a true "meat substitute," the inventor conceived of bringing in pea protein to provide the protein. However, the inventor found that it was difficult to add the pea protein to the konjac, and, in some cases, the mixture fell apart. The inventor discovered that by adding in fenugreek the pea protein could be merged with the konjac to make a homogenous material for patties and fillets. In this way the inventor has been able to create a meat replacement product that has good fiber and protein content. Hemp may also be utilized in accordance with the present invention. In this regard, hemp is used to replace soy or pea as the main plant-based protein.

In accordance with one aspect of the present invention, a meat replacement food product is provided. The meat replacement food product includes konjac and at least one vegetable-based protein source combined so as to yield a cohesive mixture that can be formed into a desired shape. In a preferred implementation, the vegetable-based protein source is pea protein. In addition, a binding agent may be provided for assisting in forming the pea protein and konjac into the cohesive mixture. The binding agent is preferably fenugreek, possibly in combination with pea starch or potato starch. The resulting meat replacement food product is soy free and can be formed into any desired shape such as filet, patty, fish stick, shrimp shape, scallop shape, calamari ring, or others.

The products produced according to the present invention are suitable for use as meat substitutes. This entails both aesthetic qualities and nutritional qualities. With regard to aesthetic qualities, an important quality is to have a texture like meat-based products. The texture of traditional meat-based products varies from fish to chicken to beef or pork and from fillets to meat chunks to ground meat products. In general, though, consumers desire that meat substitutes have a texture similar to traditional meat in terms of cohesiveness or stickiness, crumb size, structure or tenderness, and water content or juiciness. Additional aesthetic qualities of importance include appearance and flavor or ability to absorb or take-up a flavor additive. In each case, a meat substitute should reasonably replicate the meat being replaced, e.g., beef filet, ground beef, tuna, shrimp, etc.

It is also important that meat substitutes reasonably replicate the healthful nutritional qualities of meat products, generally without the unhealthful qualities of some meat products. In this manner, traditional recipes can be prepared with meat substitutes and yield nutritional value at least equal to the original meat-containing recipes. An important healthful nutritional quality of meats is high protein content. Protein is an essential component of a healthful diet for humans and other animals. Meats such as fish, poultry, pork, and beef typically provide about 20-30 grams of protein in a 100 gram serving. Stated differently, they provide a protein density (protein mass/total mass) of about 20-30%. It is therefore desirable that a meat substitute have a protein density of between about 10-40% and, more preferably, between about 20-30%, so that the meat substitute is a suitable substitute for meat in terms of nutrition and consumers will receive approximately the expected nutritional benefits. It can be difficult for vegans to obtain the needed protein in their diets, and it is even more difficult to get the needed protein in satisfying forms, particularly for those who desire meat-like products, without relying on soy or GMO foods.

In accordance with one aspect of the present invention, a meat replacement food product is provided. The meat replacement food product includes konjac and at least one vegetable-based protein source combined so as to yield a cohesive mixture that can be formed into a desired shape. In a preferred implementation, the vegetable-based protein source is pea protein. In addition, a binding agent may be provided for assisting in forming the pea protein and konjac into a cohesive mixture. The binding agent is preferably fenugreek, possibly in combination with pea starch or potato starch. The resulting meat replacement food product is soy free and can be formed into any desired shape such as filet, patty, fish stick, shrimp shape, scallop shape, calamari ring, or others.

In accordance with another aspect of the present invention, a pea protein product is extruded to yield a soy-free meat substitute. As noted above, pea protein is difficult to extrude and has generally not been used to yield meat replacement products. In particular, because pea protein has short fibers and is less cohesive or sticky than soy, it is difficult to extrude and does not readily yield a suitable meat substitute. The present invention provides a product and a process where pea protein is combined with one or more vegetable-based, non-soy binding agents and processed such that the combined pea protein binding agent are extrudible to provide a meat substitute. The meat substitute is preferably vegan and free of GMOs.

In one implementation, the pea protein is combined with konjac and/or fenugreek prior to extrusion. In particular, it has been found that the combination of konjac, pea protein, and fenugreek provides a meat substitute that is extrudible, has a desirable meat-like texture and appearance, has a suitable protein content for a meat substitute, and also provides a good source of fiber. The product can be readily processed to provide a variety of meat substitute products including meatless shrimp, tuna, and salmon-substitute, and a variety of meatless patties and filets, as well as meatless fish sticks. In order to facilitate extrusion, the pea protein/binder combination may be subjected to heat and pressure treatment prior to extrusion as described below.

In accordance with another aspect of the present invention, konjac is combined with a vegetable protein to produce a meat substitute. Konjac is a high fiber plant without protein; it generally has not been combined with vegetable-based proteins and has not been used in meat substitutes. In the inventive product and process, konjac is combined with a vegetable-based protein, preferably a non-soy protein source such as pea protein or hemp. A further agent may be used to promote such combinations such that the vegetable-based protein is embedded in the konjac to provide a cohesive meat substitute product. For example, fenugreek has been found to promote the combination of konjac with pea protein to yield a soy-free meat substitute of excellent quality.

In accordance with another aspect of the present invention, a method is provided for use in producing a meat replacement food product. The process involves preparing a first mixture of konjac flour and water. For example, the konjac flour and water may be mixed in a ratio of 1 part konjac flour to about 20-30 parts water. The method further involves adding pea protein to the first mixture and processing the first mixture together with the pea protein to form a second mixture. This processing may include adding fenugreek as well as pressure and temperature treatment. The method further involves extruding the second mixture to yield an intermediate product (TVP or textured vegetable protein) which can be used to make a final meat replacement product. In some cases, these textured vegetable proteins may be rehydrated, dehydrated, mashed, mixed with seasonings and/or binders, shaped into forms of the meat alternatives, and finally baked or fried. In other cases the product may be processed to provide a smoked flavor. In any event, the final product can then be packaged and shipped.

In accordance with a still further aspect of the present invention, a method is provided for processing pea protein so that is it is rendered extrudible. As noted above, pea protein has not previously been susceptible to extrusion. The method involves providing a pea protein component by mixing the pea protein component with at least one other vegetable-based component to form a first mixture; and adding water to the first mixture and heating the first mixture under pressure to form an extrudible mash. The step of mixing may involve combining the pea protein with a konjac flour component. The mixing may further involve utilizing a binding agent. In a preferred implementation, the binding agent comprises fenugreek. It has been found that the binding agent allows the pea protein to bind with the konjac flour component to form the desired extrudible mash.

BRIEF DESCRIPTION OF THE DRAWINGS

For a more complete understanding of the present invention, and further advantages thereof, reference is now made to the following detailed description, taken in conjunction with the drawings, in which.

DETAILED DESCRIPTION

The invention sets forth a new vegan meat replacement platform which delivers fiber and protein content, superior meat-like texture, can be formed into patties and fillets of any shape, can be extruded into respective textures, and is free from any GMO ingredients. The product has been made into burgers, fillets, prawns, vege-salmon, and canned as vege-tuna to date, and can be used to produce many meat replacement products. Various inventive products and processes are described below to illustrate the principles of the invention. It will be appreciated that many other products and processes are possible in accordance with the invention.

The Vegan Meat-Replacement Product Method

Traditionally, meat-replacement products have been made by creating and forming texturized vegetable protein (mostly grain or legume) with defatted plant flours or concentrates, such as soy protein concentrate, that are mechanically processed by extruders to obtain meat-like chewy texture when they are rehydrated and cooked. Largely, these texturized vegetable proteins have been made with isolated soy protein concentrate, soy flour, and corn starch, or less commonly, with isolated wheat protein concentrate, wheat flour, and corn starch Soy protein is a highly nutritious food and it contains the eight essential amino acids that are required for human nutrition. But soy has become highly controversial due to the widespread introduction of genetically modified soybean crops. Among other things, this invention rethinks how to make vegan meat-replacement products by turning both to alternative ingredients, most notably konjac and pea protein, and new methods of processing foods.

The Manufacturing Process

Figure 1:
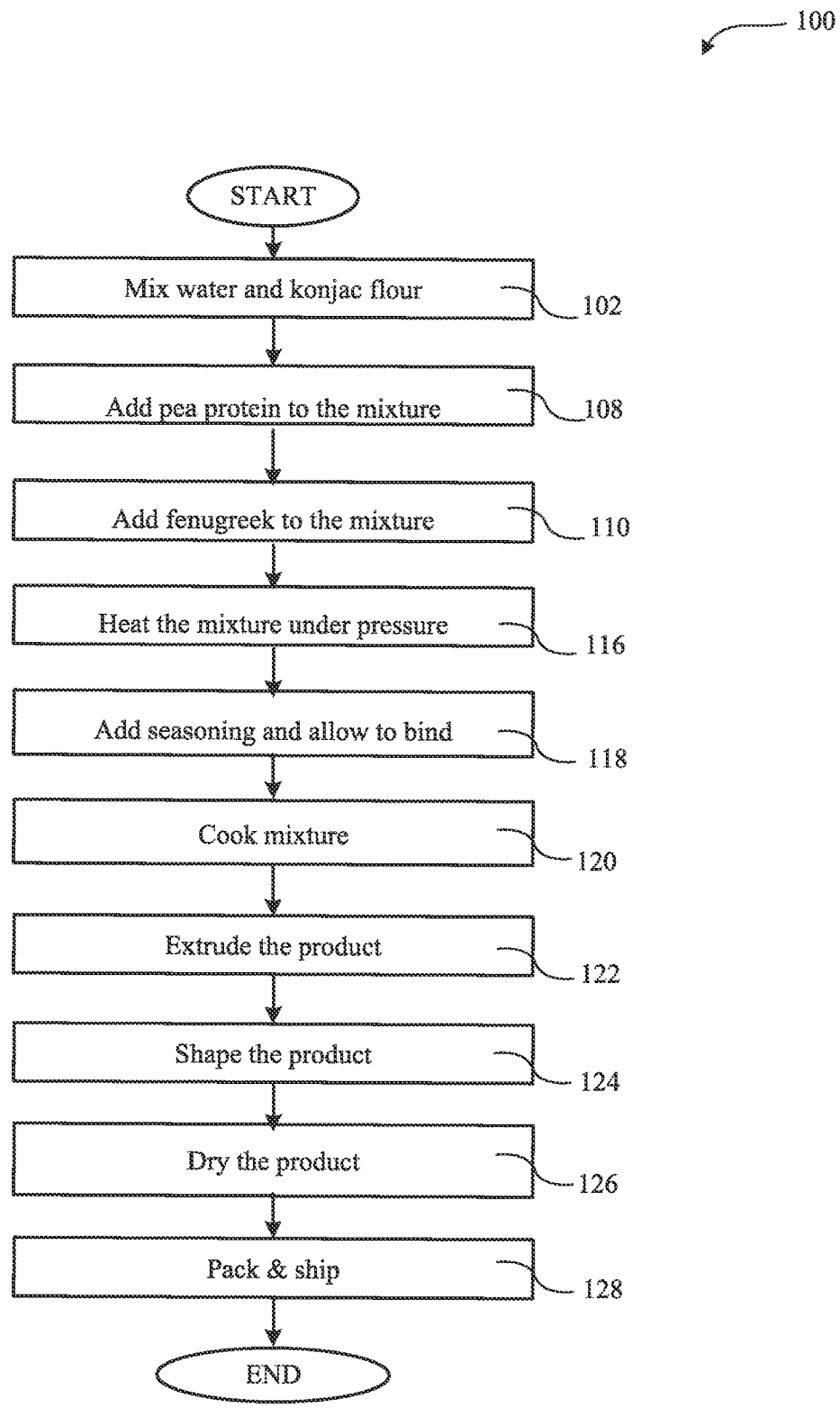
FIG. 1 is a flowchart illustrating a process for making meat replacement product in accordance with the present invention.

A preferred process and facility in accordance with the invention are shown in the flowchart of FIG. 1 and schematic diagram of FIG. 2, and are described below. It will be appreciated that the specific steps, and sequence of steps, are provided by way of example and may be varied in accordance with the present invention.

A. Mixing

As noted above, the present invention preferably utilizes a non-soy vegetable protein, together with certain binding agents, to yield a high-quality vegan meat replacement free from GMOs. In a preferred implementation, pea protein is selected as the basic protein source. Because pea protein is difficult to extrude and provide in a form that has a suitable meat texture, additional ingredients are utilized in the present invention to make meat replacement product, and certain pre-processing of the combined ingredients is performed to facilitate extrusion. In the process illustrated in FIG. 1, the pea protein is combined with konjac and fenugreek and the combination is subjected to high pressure and temperature in conjunction with the extrusion and texturization process. The specific steps that follow have yielded excellent results though different combinations, steps, and sequencing could be utilized.

Referring to FIG. 1, the illustrated process 100 is initiated by mixing (102) konjac flour and water. The ratio of flour to water as well as the mixing time and temperature can vary somewhat, and there is some interplay between these elements. In this regard, the ratio of konjac flour to water is preferably 1 part flour to 20-40 parts water and the initial mixing may be performed in a mixing vat 204 (FIG.) that preferably includes mixing paddles or blades. The time and temperature employed can be varied depending on the desired product.

An important aspect of this process is the use of konjac flour. Whey protein, egg white, or enzymes are used traditionally in the making of vegetarian meat alternatives in order to bind the textured vegetable protein. However, while "vegetarian" products can admit of certain animal products that did not result in the death of the animal, "vegan" foodstuffs adhere to a stricter standard that eliminates all animal products. Therefore the inventor steered away from any use of whey protein, egg whites, or enzymes, such as beta glucan or curdlan gum which are yeast extracts that are used as binding agents that are largely cultivated with GMO corn. Konjac flour was recognized the best and the rarest choice as binding agent. It also helps to elevate the overall fiber counts in the resulting products, making the products nutritionally more valuable.

The konjac flour and water are mixed at a ratio of 1 part konjac flour to 20-40 parts konjac flour. Particularly good results have been achieved using a mixture of 1 part konjac flour to 30-40 parts water and allowing it set for 5 minutes at over 140° C.

B. Preconditioning:

There are many physical and chemical differences between soy and pea protein. The key differences in this new process between making a textured vegetable protein out of soy and out of pea protein are mostly the novel processes that are undertaken to precondition the mixture, extrude it, and in shaping.

Preconditioning is undertaken to: i) improve moisture penetration, ii) improve heat transfer, iii) obtain a higher level of gelatinization, iv) improve the ability of the mixture to receive solid and liquid ingredients, v) decrease friction/wear vi) obtain higher extruder capacities, and vii) improve the final digestibility of product.

Accordingly, certain preconditioning is required that involves adding binding agents and treating the combined ingredients under high temperature and pressure. In the illustrated process, this includes adding (108) in the pea protein to bind with the konjac. The pea protein is "processed" and "isolated" from raw peas by commercial suppliers who provide the pea protein in the form of a powder. The konjac and water mix is then mixed with pea protein powder in a 1:4 ratio or 1:5 ratio, depending on the characteristics desired for the TVP. For example, for vegan smoked salmon, the konjac and water mixture is mixed with pea protein in a 1.5 ratio.

Next, powered fenugreek is added (110). Preferably the fenugreek comprises no more than 2% and, preferably, just 1% of the total mix by weight. In some cases, the mixture is re-hydrated and allowed to set for 2-3 hours. However, in the making of TVP, the mixture of konjac and water plus pea protein plus fenugreek is not re-hydrated. Rather, that mixture is directly extruded after preconditioning. Additionally, in some cases, the liquid is drained off and the mash is allowed dry for 20-30 minutes. The pea protein has short fibers and is less sticky than soy and the mixture needs time to bind the protein to the konjac.

The combination is then heated at high temperature and pressure to prepare the mixture for extrusion. In one implementation, the mixture is heated (116) at between 120-180° C., preferably over 140° C., for between 3-5 minutes and under pressure to make the mixture more extrudible. During this heating, the combination is maintained under pressure. After this heating under pressure is complete, the process (100) continues by adding (118) seasonings, such as seaweed extracts and vinegar, and allowing the mixture bind. The mixture is then cooked (120) at 100° C. for 20-40-60 minutes depending upon the end texture desired for either a burger or a fillet. It will be appreciated that different times may be used for other products. Generally, the longer the time that the mix spends in this pre-processing, the larger the size of the finished products (TVP made out of pea plus konjac plus fenugreek). It is especially true that the making of textured pea protein can only be achieved through increased gelatinization (pea exhibits different gelatin characteristic than soy). Therefore, proper preconditioning is one of the keys in making the textured pea protein.

C. Extruding:

After the preconditioning described above, the combination is ready for extrusion. This extrusion is preferably a process of wet extrusion at high temperature, with a mechanical extrusion device (e.g., a drive screw) forcing the mixture to form the desired texture. Thus, the illustrated process (100) involves extruding (122) the mixture to create the textured product followed by cutting or crumbling to yield the desired product form. For example, an appropriate die be utilized during extrusion to provide the desired product cross-section (e.g., a narrow round or rectangular die got fish sticks or a broader die opening for fillets), and the extruded product may be cut to length for fish sticks or fillets. Moreover, the product may be extruded as a chunk to make a vege-sausage or vege-tuna, or in strips to make noodles, or in thin strips for vegan-fish products again, other textures and forms are possible depending the desired product. The different textures are achieved by controlling the extrusion parameters such as water content, temperature, pressure, processing rate (e.g., screw speed) etc. This process of cooking under pressure, moisture and elevated temperature, is effective to provide: i) texture alteration, ii) grinding, iii) thermal treatment, iv) hydration, v) partial dehydration, vi) expansion, vii) homogenization, viii) shearing, ix) protein denaturing, x) mixing, xi) gelatinization, xii) shaping, and xiii) the destruction of micro-organisms and some toxic compounds.

"Thermal treatment" is one of the most important factors during the extrusion process in making texturized pea protein. Heat generated in conjunction with pressure and moisture achieves cooking, and heat added from external sources during extrusion helps deactivate anti-nutritional factors, achieve protein denaturing, and starch gelatinization. Without the protein denaturing, it is not possible to alter the structure of pea protein or get the meat-like texture.

Without the starch gelatinization, it is not possible to get the altered pea protein to come together as crumbs. The inventor experimented with the pea protein and discovered that the making of textured pea protein requires about 25-40% more heat than would be necessary in the making of a textured soy protein. In order to achieve such high heat, the illustrated extrusion process for a textured pea protein is a "wet extrusion" process which uses external heat source rather than "dry extrusion" which only uses heat generated by the process itself.

However, too much heat is also problematic during the extrusion process. Too much heat will cause too much gelatinization which will jam the extruding machines. The art requires careful attention during the extrusion process. As the extrusion process generates heat, a temperature is monitored and the external heat source is controlled to maintain the desired temperature range.

D. Shaping:

As noted above, the extrusion process can yield chunks, strips, crumbs or other textures depending on the desired product. This extruded material is generally malleable, cohesive, and somewhat sticky, when processed as described above, and is amenable to shaping (124) to from desired product shapes such as sticks, fillets, and the like.

However, shaping of textured pea protein is also different from the shaping of textured soy protein. This again is due to the fact that pea exhibits very different gelatin-like characteristics than soy. Therefore, it cannot be made into different shapes and sizes easily like texturized soy protein and careful control of the extrusion parameters and handling is required.

E. Drying and Baking/Frying:

The product is then dried (126) in preparation for cooking or frying. The product can then be breaded and fried or baked, as in fish sticks.

F. Packing:

A variety of finishing and packing (128) processes can then be performed depending on the nature of the end product. For example, some products are canned in oil (e.g., canned vege-tuna), some are boxed or bagged (e.g., fish sticks and pre-cooked filets), and some are wrapped for use as a meat replacement ingredient in various recipes. Importantly, the manufacturing process for vegan tuna differs in that at the end of the process the final pre-cook vege "meat chunk" made from previous process are put into cans, which are then filled with olive oil and closed.

In the manufacturing process for Vegan Smoked Salmon, konjac flour is mixed with paprika and fenugreek powder and water to make an initial mixture, mixture A. Then a second mixture is created with konjac flour, pea protein powder, fenugreek powder and water to create mixture B.

The mixtures A and B are poured into separate molds and cooked for 10 minutes at 100° C., or until the cooked mixture becomes mushy. Then mixture A is poured into another mold a few layers at a time. And in the interval of some layers, one layer of mixture B is added in between the mixture A layers. This will help create the unique color pattern seen on the salmon meat. Finally, this mixture of A plus B is put into the oven and baked for another 20 minutes at 100° C. After baking, the new mixture will come out just like a salmon steak. Then, this steak is sliced to the desired thickness. The slices can be placed into natural wood smoke machines for smoky flavor and darker color. After this, the product is then finished and ready for packing.

Processes as generally described above can be used to produce meat-free, vegan crab cakes (gluten-free), fish fillets, calamari, shrimp, prawns (gluten-free), fishless sticks (gluten-free), coconut shrimp (gluten-free), and smoked salmon, among other products.

Figure 2:
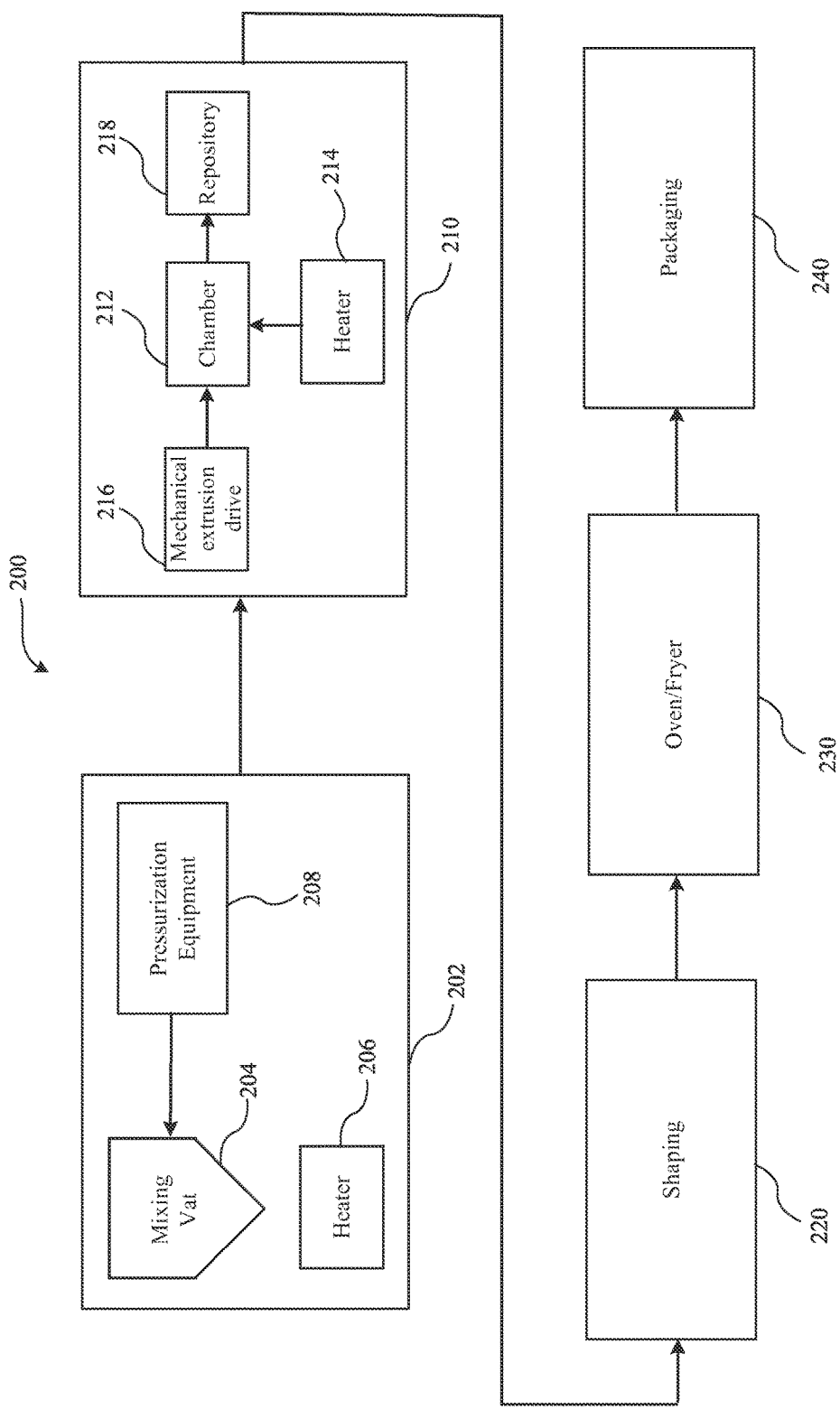
FIG. 2 is a schematic diagram of a manufacturing facility for making a meat replacement product in accordance with the present invention.

FIG. 2 is a schematic diagram of a processing facility 200 that can be used to make meat replacement products in accordance with the present invention. Various details will change depending on the product (e.g., is it baked or fried?). Is it canned or boxed?). In addition, the functionality described can, in many cases, either be performed by separate machines or combined into a single piece equipment. For example, as noted above, both the preprocessing and the extrusion processes involve heating under pressure and a single piece of equipment can be configured to perform both of these processes. In FIG. 2, the facility 200 is depicted as schematically including separate pieces of equipment for these functions. While this facilitates the present description, it will be appreciated that physically separate machines are not required in accordance with the present invention.

The illustrated facility 200 schematically includes a preprocessing machine 202 and an extrusion machine 210. The preprocessing machine 202 is used to mix the ingredients (water, konjac flour, pea protein powder, fenugreek, flavorings, etc.) and to heat the mixture under pressure as described above. Accordingly, the illustrated preprocessing machine 202 includes a vat 204 for receiving the ingredients, a heater 206 for heating the contents of the vat 204. The vat 204 may have paddles, blades and/or other mixers to mix and circulate the ingredients, e.g., to keep the solids from settling to the bottom of the vat. Although not shown, the preprocessing machine includes controls for controlling the heater 206, pressurization equipment 208, and mixers or other components of the vat 204. The vat 204 may further include valves, pumps, conduits, and other plumbing for injecting water and extracting the preprocessed mixture, as well as hatches or other ports for introducing the solid ingredients.

The illustrated extrusion machine 210 includes an extrusion chamber 212, a heater 214, a mechanical extrusion drive 216, and a repository 218 for collecting the extruded textured vegetable protein product. The extrusion chamber 212 receives the preprocessed mixture from the preprocessing machine 202. The heater 210 can then be operated to bring the mixture to the desired temperature, and maintain the mixture at the desired temperature, for the extrusion process. In this regard, a controller of the extrusion machine 210 can receive feedback temperature readings from a sensor in the chamber 212 and control the heater 214 in response to the readings to achieve and maintain the desired temperatures. The extrusion machine 210 may further include water inlets to introduce the desired moisture content for the wet extrusion process. Again, this may be controlled in response to humidity or moisture sensors in the extrusion chamber 212.

The mechanical extrusion drive 216 is operative to pressurize the mixture in the chamber 212 and to mechanically force the mixture so as to provide the desired texture. Various types of drive mechanisms and associated componentry may be utilized depending on the desired texture. For example, the mechanical extrusion drive 216 may include a screw drive, a piston, one or more dies, and blades or scrapers for cutting the product extruded through the die. The texture resulting from this extrusion is due, among other things, to protein denaturation, starch gelatinization, die configuration, and cutting. Various textures can be achieved by controlling the composition and particular size of the ingredients/mixture; the temperature, pressure, and mixture content during extrusion the feed rate of the mixture and water; and the screw speed (or other operating rate) of the extrusion drive. The textured vegetable product is deposited in the repository 218 upon being expelled from the extrusion chamber 212.

The textured vegetable product is then delivered (manually or automatically) from the repository of the extrusion machine 200 to the shaping machinery 220. The shaping machinery 220 forms the textured vegetable product into the desired shape. The desired shape will vary from product-to-product, e.g., vege-tuna, vege-shrimp, filets, chunks, fish sticks, etc. In this regard, the textured vegetable product may be pressed into molds, cut, ground, breaded, etc. In some cases, additives, heating and mechanical processing may be needed to force the product to assume and maintain the desired shape, in all cases consistent with the desired characteristic of the end product (e.g., vegan, soy-free, GMO-free, dairy-free, etc.).

In some cases, the desired end product is baked or fried and, in other cases, no cooking is required (other than that entailed in preprocessing and extrusion). Where cooking is necessary, the product can be manually or automatically delivered from the shaping machinery 220 to an oven or fryer 230. It will be appreciated that such cooking may be desired yield a fully-cooked, ready-to-eat product, or to achieve drying, partial-cooking, cohesion enhancement or other effects. The cooked product (or uncooked product) is then ready for packaging by the packaging machine 240. Depending on the product, this may involve canning, bagging, wrapping, etc.

The foregoing description of the present invention has been presented for purposed of illustration and description. Throughout this description, heat and pH are critically controlled and any variation greatly influences the quality of the final product. Furthermore, the description is not intended to limit the invention to the form disclosed herein. Consequently, variations and modifications commensurate with the above teachings, and skill and knowledge of the relevant art are within the scope of the present invention. The embodiments described herein above are further intended to explain best modes known of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed:

1. A method for producing a vegan meat replacement food product, comprising the steps of:
    mixing konjac flour and water in a ratio of 1-part konjac flour to about 20-40 parts water,
    adding a non-soy vegetable protein comprising pea protein powder to the konjac flour and water mixture in a ratio of one part of the konjac and water mixture to 4 or 5 parts non-soy vegetable protein;
    adding fenugreek powder to form a mixture, wherein the fenugreek powder is at a level of 1-2% by weight of the mixture;
    applying heat and pressure to the mixture, and
    extruding and shaping the mixture to form a vegan meat replacement product, wherein the fenugreek facilitates the binding of the non-soy vegetable protein to the konjac flour.

2. The method of claim 1, wherein the mixture is heated at between 120-180° C. for a time period of between 3-5 minutes.

3. The method of claim 1, wherein after the applying heat and pressure step, the mixture is baked at a temperature of 100° C. for 20-60 minutes.

* * * * *